US008303902B2

(12) United States Patent
Kim

(10) Patent No.: US 8,303,902 B2
(45) Date of Patent: Nov. 6, 2012

(54) SLIDE PROCESSING APPARATUS

(75) Inventor: Byung-Chul Kim, Yongin-si (KR)

(73) Assignee: Samsung Electronics Co., Ltd., Suwon-Si, Gyeonggi-Do (KR)

(*) Notice: Subject to any disclaimer, the term of this patent is extended or adjusted under 35 U.S.C. 154(b) by 532 days.

(21) Appl. No.: 12/547,214

(22) Filed: Aug. 25, 2009

(65) Prior Publication Data

US 2010/0055006 A1 Mar. 4, 2010

(30) Foreign Application Priority Data

Aug. 26, 2008 (KR) ........................ 10-2008-0083517

(51) Int. Cl.

| | |
|---|---|
| ***B01J 19/00*** | (2006.01) |
| ***B01L 9/00*** | (2006.01) |
| ***B01L 3/00*** | (2006.01) |
| *B65D 25/04* | (2006.01) |
| *B65D 85/48* | (2006.01) |
| *C12M 1/00* | (2006.01) |

(52) U.S. Cl. ........ 422/198; 422/552; 422/554; 422/547; 422/559; 422/563; 422/536; 435/91.2; 435/289.1; 206/456; 220/544

(58) Field of Classification Search ........................ None
See application file for complete search history.

(56) References Cited

U.S. PATENT DOCUMENTS

| | | | | |
|---|---|---|---|---|
| 6,225,109 | B1 * | 5/2001 | Juncosa et al. | 435/288.5 |
| 2001/0003652 | A1 * | 6/2001 | Freeman | 435/286.5 |
| 2006/0210451 | A1 * | 9/2006 | Anderson et al. | 422/104 |
| 2006/0275889 | A1 * | 12/2006 | Angros et al. | 435/287.1 |

FOREIGN PATENT DOCUMENTS

| | | |
|---|---|---|
| JP | 10-090145 | 4/1998 |
| KR | 10-0313903 | 10/2001 |
| KR | 20-0235153 | 10/2001 |
| KR | 20-323025 | 8/2003 |
| KR | 10-0408167 | 11/2003 |
| KR | 100743225 | 7/2007 |

OTHER PUBLICATIONS

English Abstract for Publication No. 10-090145.
English Abstract for Publication No. 20-0235153.
English Abstract for Publication No. 1020010039377 (for 10-0313903).
English Abstract for Publication No. 20-323025.
English Abstract for Publication No. 1020020088838 (for 10-0408167).
English Abstract for Publication No. 100743225.

* cited by examiner

*Primary Examiner* — In Suk Bullock
*Assistant Examiner* — Jennifer Wecker
(74) *Attorney, Agent, or Firm* — F. Chau & Associates, LLC

(57) ABSTRACT

Provided is a slide processing apparatus for processing a plurality of slides to which a bio probe is attached. The slide processing apparatus includes a reaction chamber of which side walls are sealed, and a plurality of reaction heating plates disposed in parallel in the reaction chamber at a first distance from each other. The slides are mounted adjacent to the reaction heating plates in the reaction chamber and in parallel to the reaction heating plates.

15 Claims, 8 Drawing Sheets

SLIDE PROCESSING APPARATUS

CROSS-REFERENCE TO RELATED APPLICATIONS

This application claims the benefit of Korean Patent Application No. 10-2008-0083517, filed on Aug. 26, 2008, in the Korean Intellectual Property Office, the contents of which are herein incorporated by reference in their entirety.

BACKGROUND

1. Field of the Invention

The present disclosure is directed to a slide processing apparatus, and more particularly, to a slide processing apparatus capable of simultaneously processing a plurality of slides to which a bio probe is attached.

2. Discussion of the Related Art

In line with biotechnology advancements, various types of bio chips have been developed. Bio chips may be classified into gene chips, protein chips, cell chips, etc., according to the types of living materials incorporated into the chip. For example, a deoxyribonucleic acid (DNA) probe is attached to the surface of a DNA chip. In addition, a protein, such as an enzyme or an antigen/antibody, bacteriorhodopsin, etc., may be attached to the surface of a protein chip.

In these bio chips, a bio probe is attached to the surface of a slide, such as a glass slide. A reaction may be performed on the bio chip by using a reactant sample, such as a solution that reacts with a bio probe on a slide, and the result is analyzed after a long-term incubation process. Also, if needed, a plurality of bio probes of different types may be attached to the surface of a slide so that various results can be obtained.

SUMMARY

One or more exemplary embodiments of the invention include a slide processing apparatus capable of simultaneously processing a plurality of slide-type bio chips to which a bio probe is attached, and in particular, include a slide processing apparatus capable of simultaneously processing a plurality of bio chips in which a limited reaction sample is used or reaction temperature can be easily controlled.

One or more exemplary embodiments may include a slide processing apparatus for processing a plurality of slides in which a bio probe is integrated, the slide processing apparatus including: a reaction chamber of which slide walls are sealed; and a plurality of reaction heating plates disposed in parallel in the reaction chamber at a first distance from each other, wherein the slides are mounted adjacent to the reaction heating plates in the reaction chamber and in parallel to the reaction heating plates.

Each slide may include a first side and a second side opposite to the first side, and a bio probe may be attached to the first side of each slide. Each slide may be mounted toward the adjacent reaction heating plates.

The first side of each slide may be adjacent to one of the reaction heating plates.

Each slide may be mounted adjacent to one side of each reaction heating plate so that the first sides of the slides extend in the same direction as the reaction heating plate.

The reaction chamber may further include a side wall heating plate inside the side walls of the reaction chamber.

The side wall heating plate and each reaction heating plate may be connected to each other.

The reaction chamber may further include a first slot in which each slide is mounted inside the side walls of the reaction chamber.

A pair of first slots may be disposed facing each other in two opposite inside areas of the side walls of the reaction chamber.

A fixing portion which fixes each slide may be attached to each reaction heating plate.

One or more embodiments may include a slide processing apparatus for processing a plurality of slide modules mounting one or more slide in which a bio probe is integrated, the slide processing apparatus including: a reaction chamber of which side walls are sealed; and a plurality of reaction heating plates disposed in parallel in the reaction chamber at a first distance from each other, wherein the slide modules are mounted adjacent to the reaction heating plates in the reaction chamber and in parallel to the reaction heating plates.

Each slide may include a first side and a second side opposite to the first side, and a bio probe may be attached to the first side of each slide.

Each slide module may include: a slide cover disposed adjacent to the first side of the slide that is to be mounted on each slide modules; and a slide clip supporting the slide and the slide cover on both ends of each slide module, wherein each slide module is mounted so that the second side of the slide mounted on the slide module is directed toward the reaction heating plates.

Each slide module may further include a spacer disposed between the slide and the slide cover so that the slide and the slide cover can be disposed in parallel at a second distance from each other.

The slide clip may include a second slot in which the slide and the slide cover are mounted at the second distance from each other.

A plurality of slides may be mounted in each slide module; and the first sides of the slides may be placed in parallel in the same direction.

A reaction space which is encompassed by the slides, the slide cover, and the slide clip, may have a volume of about 10 µl to about 1 Ml.

The first distance may be about 0.5 cm to about 2 cm.

DETAILED DESCRIPTION OF EXEMPLARY EMBODIMENTS

Figure 1:
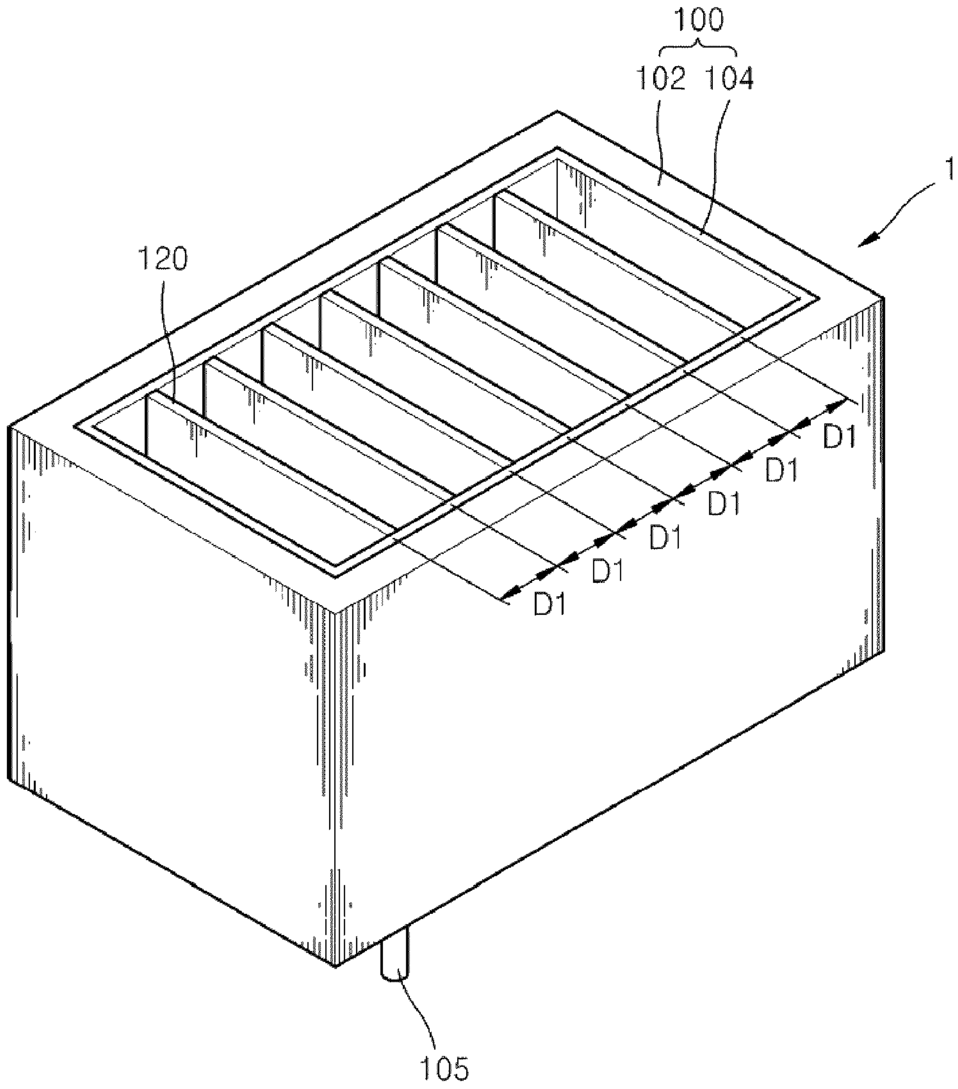
FIG. 1 is a schematic perspective view of a slide processing apparatus according to an embodiment of the invention.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. In the drawings, the thicknesses of layers and regions are exaggerated for clarity. It will also be understood that when a layer is referred to as being "on" another layer or substrate, it can be directly on the other layer or substrate, or intervening layers may also be present.

FIG. 1 is a schematic perspective view of a slide processing apparatus 1 according to an embodiment of the invention.

Referring to FIG. 1, a slide processing apparatus 1 according to the current embodiment of the invention includes a reaction chamber 100 and a plurality of reaction heating plates 120. Side walls of the reaction chamber 100 are sealed. The reaction chamber 100 may include a chamber cover 102 and a side wall heating plate 104. The side wall heating plate 104 is attached to the chamber cover 102 and is formed inside the side walls of the reaction chamber 100.

The top surface of the reaction chamber 100 may be opened, as illustrated in FIG. 1, or may be opened or closed by a separate top cover or a top cover connected to the reaction chamber 100. By using the top cover, a reaction temperature is easily maintained, and vaporization of a reaction sample can be minimized. A separate heating plate may be formed inside the top cover.

The bottom surface of the reaction chamber 100 may be sealed. A water discharge hole 105 through which a reaction sample, a cleaning solution, etc., may be discharged may be formed in the bottom surface of the reaction chamber 100.

The reaction heating plates 120 may be disposed substantially parallel to each other at a first distance D1 from each other. The first distance D1 may be determined according to the number and the size of a plurality of slides that are to be mounted, or according to a reaction sample supplying method, etc. The first distance D1 may be about 0.5 cm to about 2 cm, for example. The first distance D1 may be about 0.9 cm, for example. Each reaction heating plate 120 may adjust the degree of heating. Thus, each reaction heating plate 120 may adjust temperature of each slide mounted adjacent to each reaction heating plate 120.

The side wall heating plate 104 may be formed in side walls of the reaction chamber 100 to encompass spaces in the reaction chamber 100, which are separated from one another by the reaction heating plates 120. When the side wall heating plate 104 and each reaction heating plate 120 control temperature independently, the side wall heating plate 104 may control temperature in a wide range, and each reaction heating plate 120 may control temperature in a narrow range.

The side wall heating plate 104 and each reaction heating plate 120 may be connected to each other to control the temperature together. In this case, a reaction temperature in spaces defined by the side wall heating plate 140 and each reaction heating plate 120 can be maintained at a constant level.

The side wall heating plate 104 or each reaction heating plate 120 may control temperature in an air-cooled or water-cooled manner.

Figure 2:
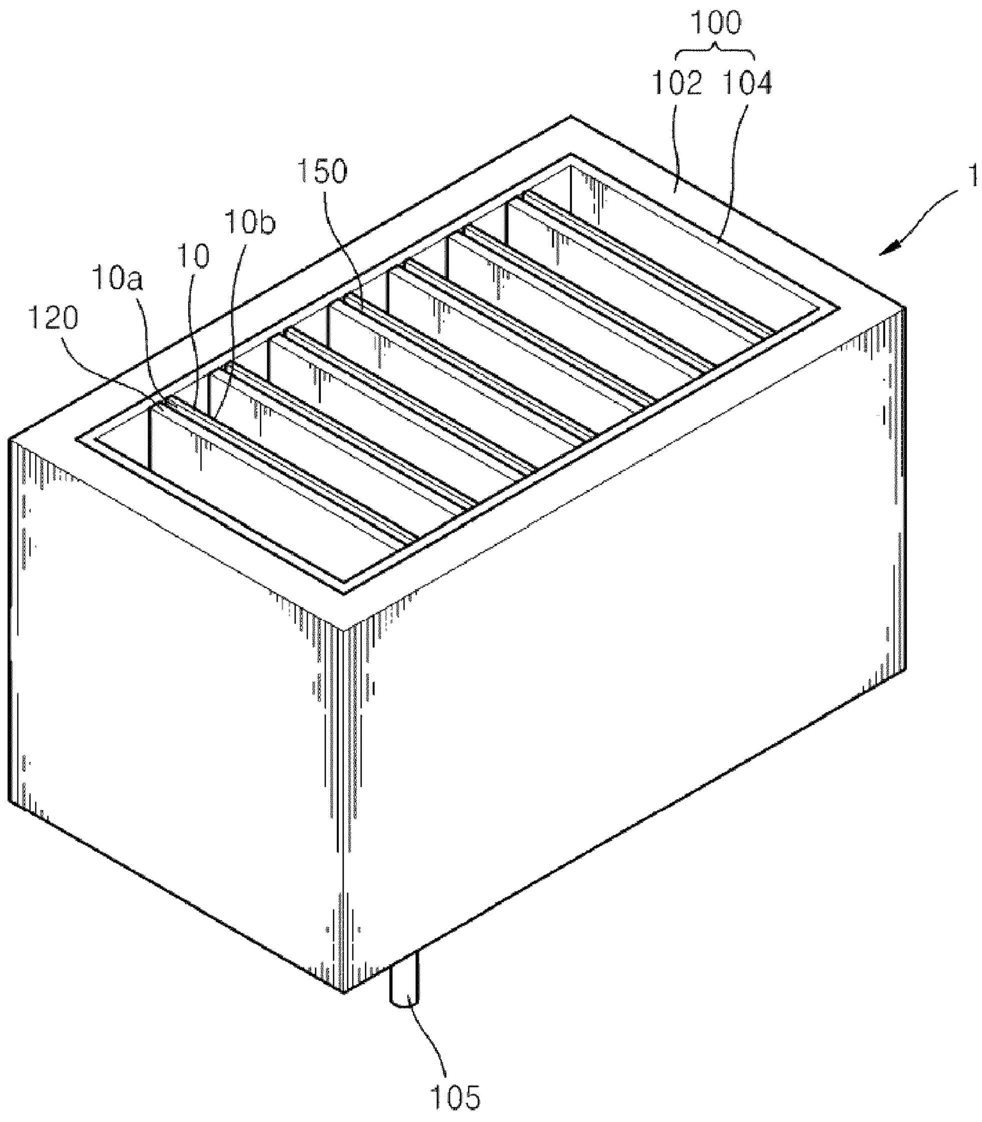
FIGS. 2 through 5 are perspective views illustrating the processing of a plurality of slides by using a slide processing apparatus according to one or more embodiments of the invention, respectively.

FIG. 2 is a perspective view illustrating the processing of a plurality of slides 10 by using a slide processing apparatus 1, according to an embodiment of the invention.

Referring to FIG. 2, slides 10 may be mounted in the slide processing apparatus 1. The slides 10 may be bio chips to which bio probes are attached. The slides 10 may include the same type or different types of bio chips. Also, the bio chips may be glass slides of the same size as the slides 10.

Hereinafter, the term "slide" indicates a bio chip to which a bio probe is attached. In addition, the term "glass slide" indicates a general slide glass plate to which a bio probe is not attached.

Each slide 10 may have a first side 10*a* to which a bio probe (not shown) may be attached, and a second side 10*b* to which a bio probe is not attached. The first side 10*a* and the second side 10*b* may have the area of about 3 inch×about 1 inch, for example.

Each slide 10 may be mounted adjacent to one side of the reaction heating plates 120 so that the side extends in the same direction as the reaction heating plates 120. In this case, the first side 10*a* of each slide 10 may be mounted to face each reaction heating plate 120. A reaction space 150 may be formed between each slide 10 and each adjacent reaction heating plate 120. A reaction sample is injected into the reaction space 150. The reaction sample can be used to process the slides 10 to which a bio probe is attached. The reaction space 150 may have a volume of about 10 μl to about 1 Ml or a volume of about 50 μl to about 200 μl.

A reaction sample may be injected into the reaction space 150 by using a pipette, etc. The reaction sample may also be injected into the reaction space 150 due to a capillary phenomenon. The reaction sample injected into the reaction space 150 may be maintained in the reaction space 150 for a duration of the reaction, and a reaction may take place continuously. Reaction samples may be simultaneously injected into a plurality of reaction spaces 150 using a multichannel pipette in which a plurality of pipettes are repeatedly arranged. When a plurality of multichannel pipettes are used, the spacing of the reaction heating plates 120 may be determined to correspond to the spacing of the multichannel pipettes.

In addition, each slide 10 is disposed adjacent to the reaction heating plates 120, which transfer heat and stably maintain a temperature required for reaction.

Figure 3:
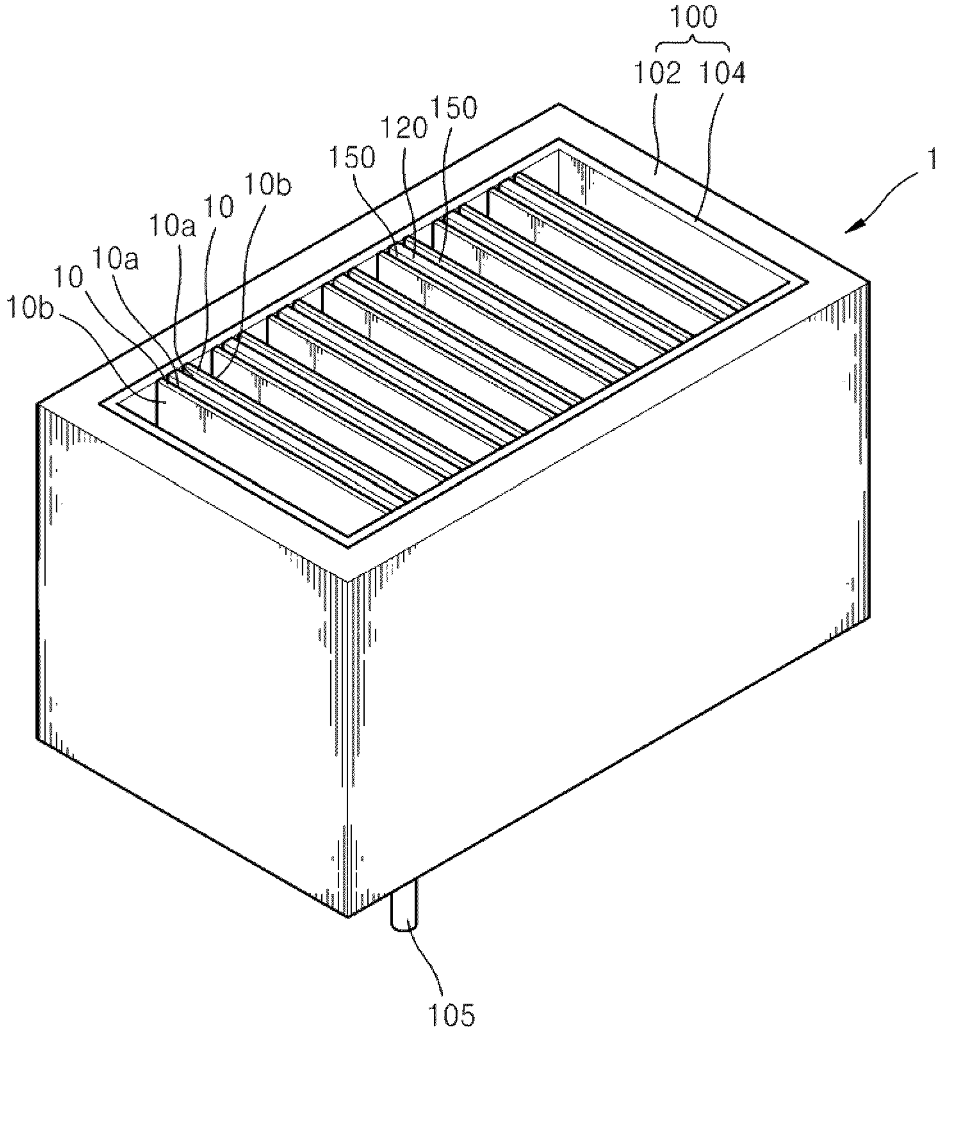

FIG. 3 is a perspective view illustrating the processing of a plurality of slides 10 by using a slide processing apparatus 1, according to another embodiment of the invention.

Referring to FIG. 3, the slides 10 to which a bio probe is attached may be disposed adjacent to both sides of each reaction heating plate 120. Each slide 10 may have a first side 10*a* to which a bio probe (not shown) is attached, and a second side 10*b* to which a bio probe is not attached. The first side 10*a* of each slide 10 may be disposed on both sides of one reaction heating plate 120 to face each reaction heating plate 120. Thus, two of the slides 10 are disposed adjacent to one reaction heating plate 120, and a reaction space 150 may be formed between each slide 10 and the adjacent reaction heating plate 120. In addition, each slide 10 is disposed adjacent to one of the reaction heating plates 120, which transfer heat and stably maintain a temperature required for reaction.

Each reaction space 150 may have substantially the same volume. To this end, a distance between the reaction heating plates 120 may be determined in consideration of the thickness of each slide 10, the thickness of each reaction heating plate 120, and the width of each reaction space 150. In this case, a reaction sample may be injected into each reaction space 150 by using a multichannel pipette including a plurality of pipettes repeatedly arranged at substantially the same distance from each other.

Although not shown, another slide may be mounted adjacent to the second side 10*b* of each slide 10 disposed adjacent to one side of the reaction heating plates 120. In other words, the first side 10*a* of each slide 10 may be disposed at both sides of one reaction heating plate 120 to face each reaction heating plate 120. In this case, each of the reaction heating plates 120 and the side wall heating plate 104 are disposed to encompass four sides of each slide 10 to maintain the temperature of each slide 10.

Figure 4:
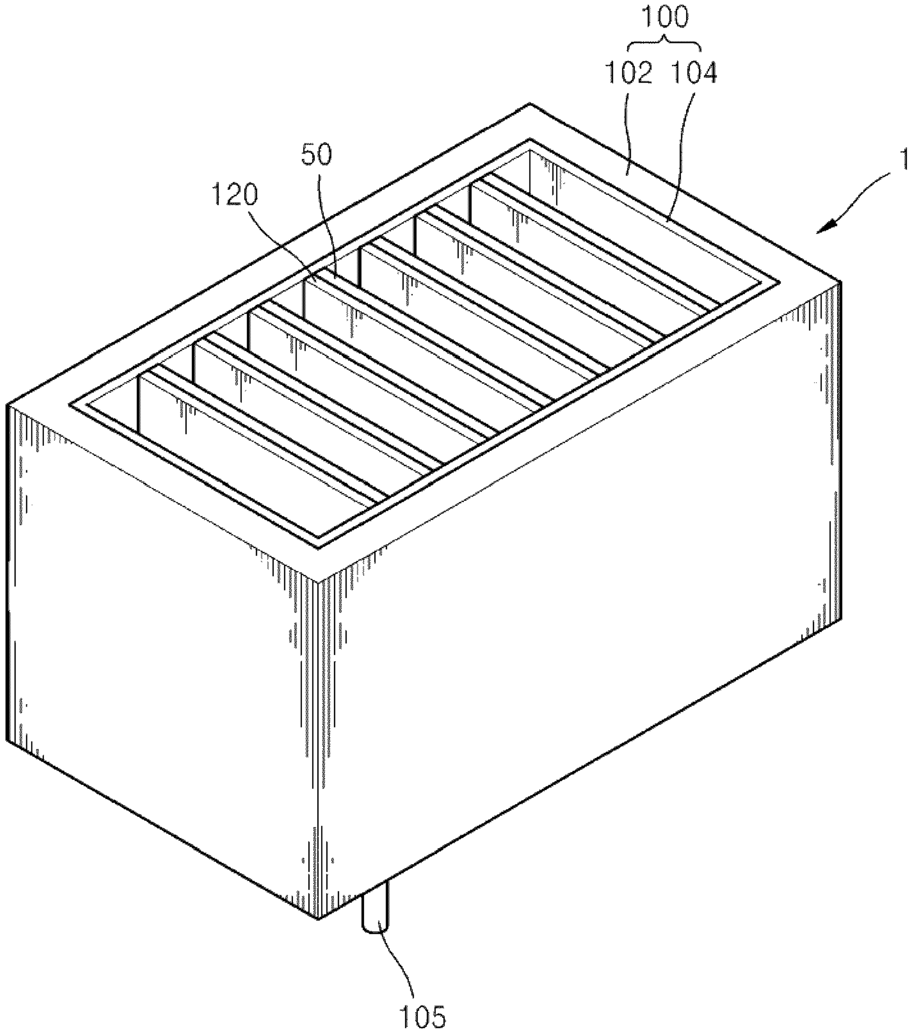

FIG. 4 is a perspective view illustrating the processing of a plurality of slides by using a slide processing apparatus 1, according to another embodiment of the invention.

Referring to FIG. 4, a plurality of slide modules 50 may be mounted in the slide processing apparatus 1. At least one slide to which a bio probe is attached may be mounted on each slide module 50.

Each slide module 50 may be mounted adjacent to one side of the reaction heating plates 120 so that the side extends in the same direction as the reaction heating plates 120. Each slide module 50 may be mounted to contact each reaction heating plate 120. However, the slides mounted on the slide modules 50 may or may not contact the reaction heating plates 120 according to the shape of each slide module 50.

A reaction space in which the slides react may be formed in each slide module 50. A reaction sample may be injected into the reaction space. The reaction sample may be injected into the reaction space either before or after each slide module 50 is mounted in the slide processing apparatus 1.

Figure 5:
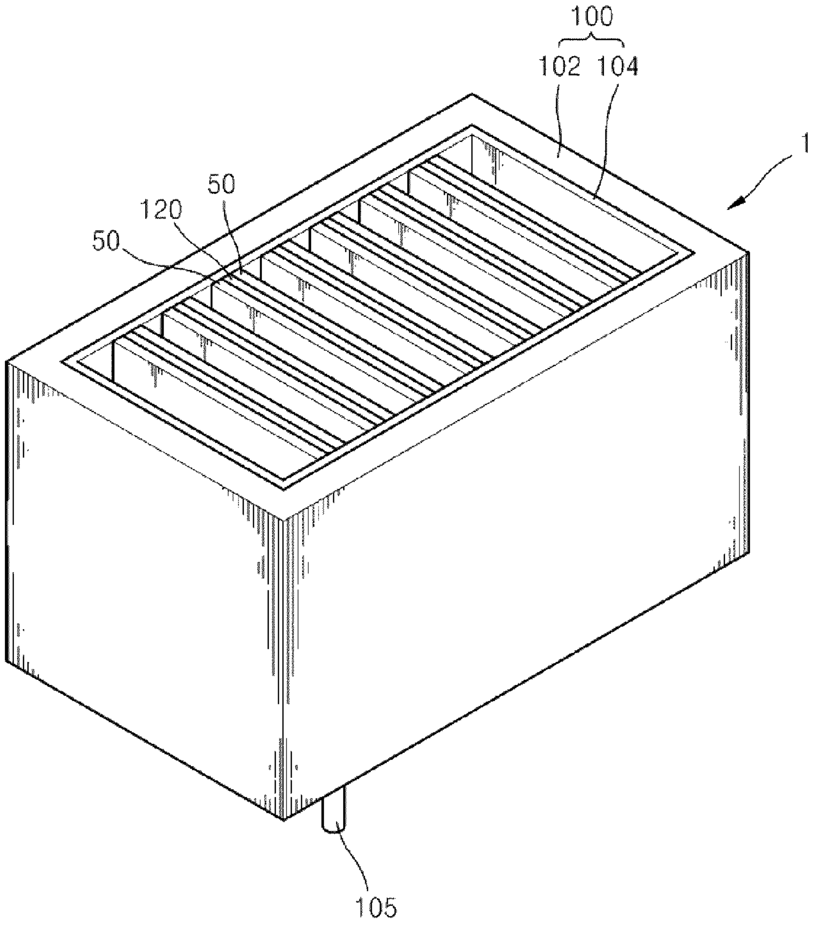

FIG. 5 is a perspective view illustrating the processing of a plurality of slides by using a slide processing apparatus 1, according to another embodiment of the invention.

Referring to FIG. 5, each of a plurality of slide modules 50 may be mounted in parallel and adjacent to both sides of a plurality of reaction heating plates 120. Each slide module 50 may be mounted to contact each reaction heating plate 120. At least one slide to which a bio probe is attached may be mounted on each slide module 50. Thus, the slide processing apparatus 1 can process more slides simultaneously.

Figure 6:
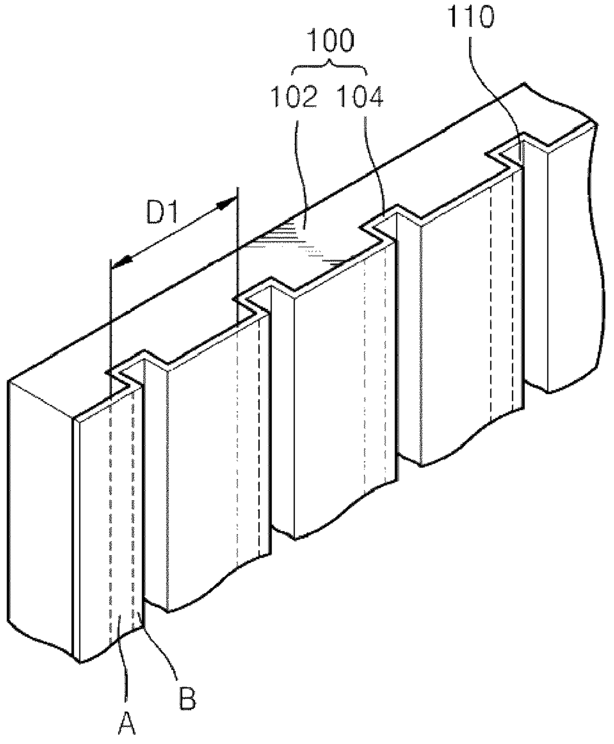
FIG. 6 is a perspective view illustrating insides of side walls of a reaction chamber included in the slide processing apparatus illustrated in FIG. 1.
Figure 7:
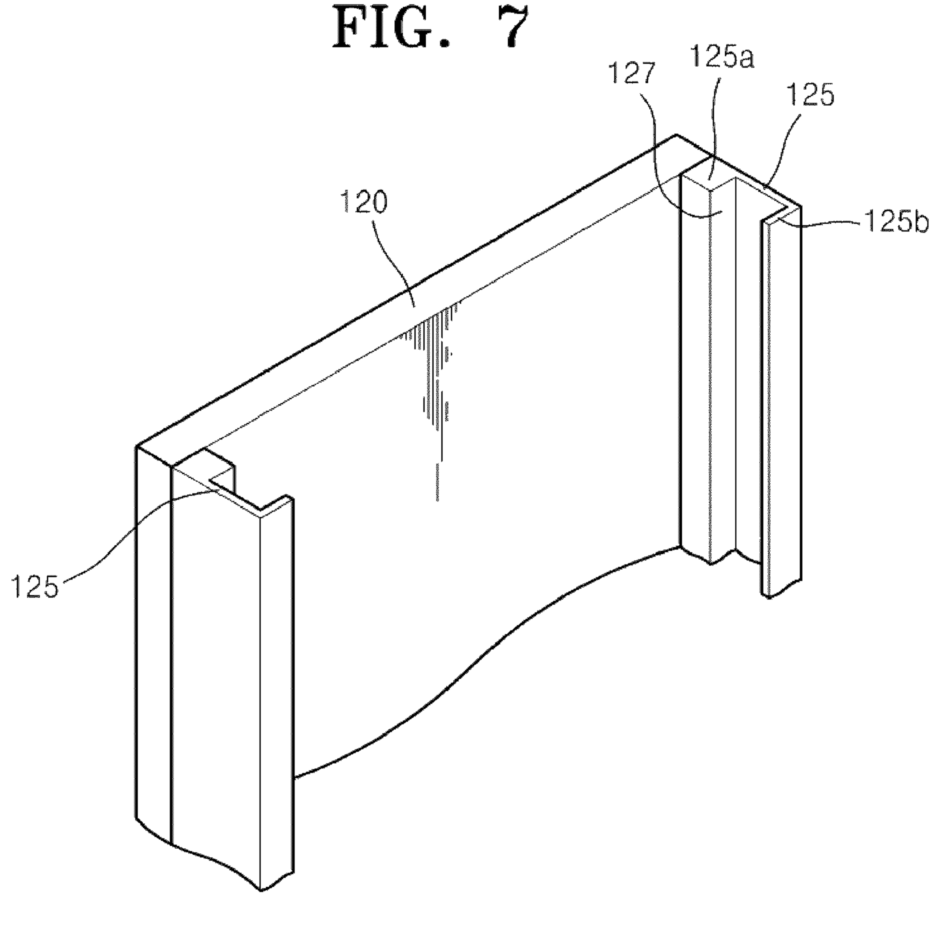
FIG. 7 is a perspective view illustrating a fixing portion attached to each reaction heating plate included in the slide processing apparatus illustrated in FIG. 1.

FIGS. 6 and 7 are perspective views illustrating portions for fixing and mounting a plurality of slides or slide modules on the slide processing apparatus 1 illustrated in FIG. 1.

FIG. 6 is a perspective view illustrating insides of side walls of a reaction chamber included in the slide processing apparatus 1 illustrated in FIG. 1.

Referring to FIG. 6, a first slot 110 is formed on the insides of the side walls of a reaction chamber 100. The first slot 110 may be formed by a groove formed in a chamber cover 102 and by a side wall heating plate 104 formed in the reaction chamber 100 including the groove, as illustrated in FIG. 6. Although not shown, the reaction chamber 100 to which the side wall heating plate 104 having the first slot 110 formed therein is attached may also be applied to the flat chamber cover 102. In other words, the first slot 110 may be formed in inner side walls of the reaction chamber 100 including the chamber cover 102 and the side wall heating plate 104 in various shapes.

A plurality of slides (not shown) to which a bio probe is attached may be mounted on the first slot 110. In this case, an additional space B in which a reaction may occur is needed between the first slot 110 and a space A to which a plurality of reaction heating plates (not shown) are attached. A plurality of modules (not shown) on which a plurality of slides having attached bio probes are mounted may be mounted on the first slot 110. In this case, the additional space B between the first slot 110 and the space A to which the reaction heating plates (not shown) are attached may be not necessary. Thus, the space A may directly contact the first slot 110 without the additional space B.

Pairs of first slots 110 may be formed facing each other in two opposite inside areas of side walls so that the slides or the slide modules can be fixed and mounted on the slide processing apparatus.

FIG. 7 is a perspective view illustrating a fixing portion attached to each reaction heating plate included in the slide processing apparatus 1 illustrated in FIG. 1.

Referring to FIG. 7, a fixing portion 125 may be formed on at least one side of each of a plurality of reaction heating plates 120. A fixing slot 127 is formed in the fixing portion 125, and a plurality of slides (not shown) or a plurality of slide modules (not shown) may be fixed in the fixing slot 127. The fixing portion 125 includes an air gap portion **125*a* and a support 125*b* so that the slides (not shown) can maintain a predetermined distance with each reaction heating plate 120. In this case, a space that is encompassed by a slide, a reaction heating plate 120, and the air gap portion 125*a* may be a reaction space. When each slide module is mounted to contact each reaction heating plate 120, the fixing portion 125 can be formed to exclude the air gap portion 125*a***.

A pair of fixing portions 125 may be formed facing each other on both ends of the reaction heating plates 120 so that the slides or the slide modules can be fixed and mounted on the slide processing apparatus 1. In addition, when the slides or the slide modules are mounted on both sides of each reaction heating plate 120, the fixing portions 125 may be formed on both sides of each reaction heating plate 120, respectively.

FIGS. 8 through 11 are top plan views illustrating the detailed structure of a slide module according to one or more embodiments of the invention, respectively.

Figure 8:
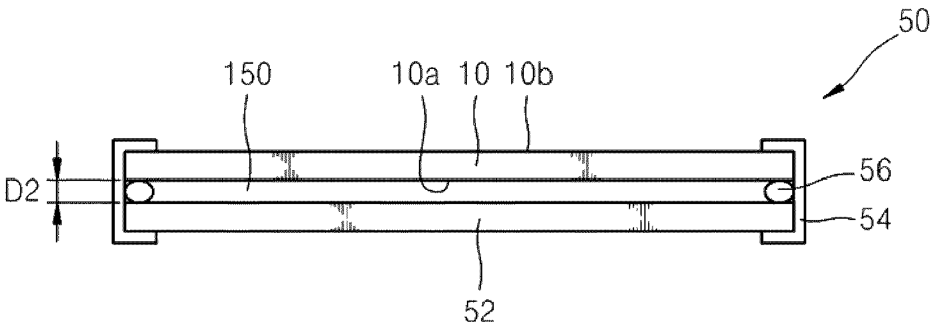
FIGS. 8 through 11 are top plan views illustrating the detailed structure of a slide module according to one or more embodiments of the invention, respectively.

FIG. 8 is a top plan view illustrating a slide module 50 on which one slide is mounted, according to an embodiment of the invention.

Referring to FIG. 8, the slide module 50 according to the current embodiment may include a slide cover 52, a slide clip 54, and a spacer 56. The slide cover 52 may be positioned adjacent to a slide 10 which is mounted on the slide module 50 and to which a bio probe is attached. The slide cover 52 may be disposed to face a first side **10*a* of the slide 10 to which the bio probes are attached. The slide cover 52** may be a glass slide, for example.

The slide module 50 may include the slide clip 54 to support the slide 10 and the slide cover 52. The slide 10 and the slide cover 52 may be supported by the slide clip 54 on both ends of the slide module 50. In addition, the slide module 50 may include the spacer 56 which maintain a second distance D2 between the slide 10 and the slide cover 52. The spacer 56 may be inserted between the slide 10 and the slide cover 52 or may be attached to the slide clip 54. The slide clip 54 may be formed of an elastic material, for example.

A reaction space 150 may be formed between the slide 10 and the slide cover 52 that is supported by the slide clip 54. The reaction space 150 may have a volume of about 10 μl to about 1 Ml or a volume of about 50 μl to about 200 μl.

The first side **10*a* of the slide 10, to which a bio probe is attached, may be disposed to contact the reaction space 150. A reaction sample may be injected into the reaction space 150 by using a pipette, etc. A plurality of reactions samples may be simultaneously injected into a plurality of reaction spaces 150 of a plurality of slide modules 50 by using a multichannel pipette in which a plurality of pipettes are repeatedly arranged. The reaction sample or samples may be positioned in the reaction space 150 via a capillary phenomenon. In addition, the reaction sample is maintained in the reaction space 150** for a duration of the reaction, which may occur continuously.

In addition, before the slide module 50 is mounted in the slide processing apparatus, the slide 10 may be mounted on the slide module 50. In other words, the reaction space 150 may be formed before the slide module 50 is mounted in the slide processing apparatus 1. Thus, the reaction sample may be injected into the reaction space 150 in advance before the slide module 50 is mounted in the slide processing apparatus 1. Thus, challenges of injecting the reaction sample into the narrow reaction spaces 150 may be overcome. In other words, after the slide 10 is mounted on the slide module 50, some or all of the slide modules 50 are immersed in the reaction sample, and the reaction sample is injected into the reaction space 150 so that the slide module 50 can be mounted in the slide processing apparatus 1. In this case, the amount of the reaction sample can be minimized, and the reaction sample can be readily injected into the reaction space 150.

The injected reaction sample may also be injected into the reaction space 150 after the slide module 50 is mounted in the slide processing apparatus.

The slide module 50 may be mounted in the slide processing apparatus 1 so that a second side 10*b* of the slide 10 mounted on the slide module 50 faces the reaction heating plate. In this regard, the slide 10 is adjacent to the reaction heating plates so that reaction temperature management including temperature control and temperature maintenance can be easily performed.

Figure 9:
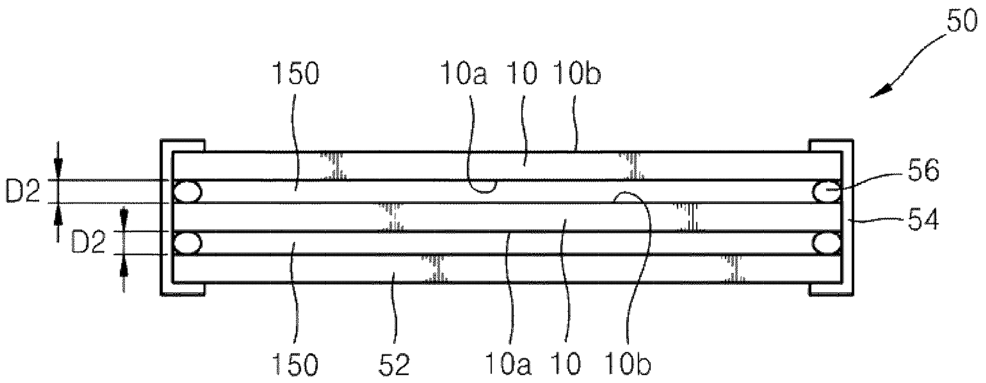

FIG. 9 is a top plan view illustrating a slide module 50 on which two slides are mounted, according to another embodiment of the invention.

Referring to FIG. 9, the slide module 50 according to the current embodiment of the invention may include a slide cover 52, a slide clip 54, and a spacer 56. At least two slides 10 may be mounted on the slide module 50. Thus, the slide module 50 may include spacers 56 corresponding to the number of slides 10 mounted on the slide module 50. In other words, the slide module 50 may include at least two spacers 56. A first side 10*a* of each slide 10 mounted on one slide module 50, may be disposed in the same direction. In other words, the first side 10*a* of each slide 10 mounted on one slide module 50 may be disposed to face the slide cover 52.

For example, when two slides 10 are mounted on one slide module 50, one reaction space 150 may be formed between the slides 10 that are adjacent to the slide cover 52, and another reaction space 150 may be formed between two slides 10.

The slide module 50 may be mounted in the slide processing apparatus 1 so that the slide 10 having a second side 10*b* directed to the outside, can be directed toward the reaction heating plates.

Figure 10:
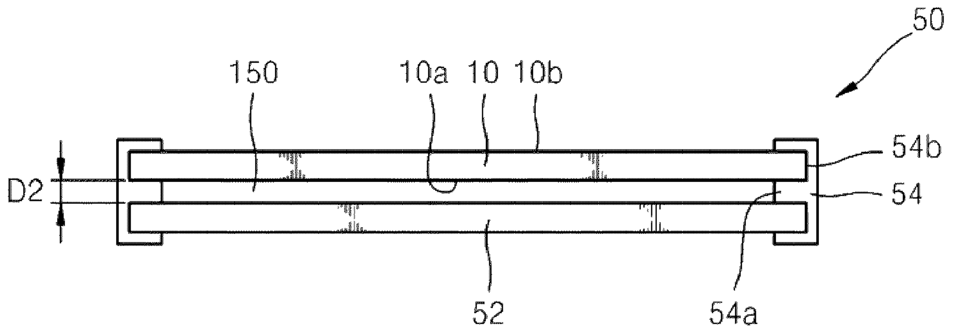

FIG. 10 is a plan view illustrating a slide module 50 on which one slide is mounted, according to another embodiment of the invention.

Referring to FIG. 10, the slide module 50 according to the current embodiment of the invention may include a slide cover 52 and a slide clip 54. The slide cover 52 may be positioned adjacent to a slide 10 to which a bio probe is attached, so that the slide cover 52 faces a first side 10*a* of the slide 10.

The slide module 50 may include the slide clip 54 to support the slide 10 and the slide cover 52. The slide 10 and the slide cover 52 may be supported by the slide clip 54 on both ends of the slide module 50. A reaction space 150 may be formed between the slide 10 and the slide cover 52 that are supported by the slide clip 54. The slide clip 54 may include a clip air gap portion 54*a* which maintains a second distance D2 between the slide 10 and the slide cover 52, and a pair of second slot 54*b* on both ends of the slide module 50 which fix and support the slide 10 and the slide cover 52.

With this structure, the slide module 50 may include a reaction space 150 that is formed between the slide 10 mounted on the slide module 50, the slide cover 52, and the slide clip 54.

Figure 11:
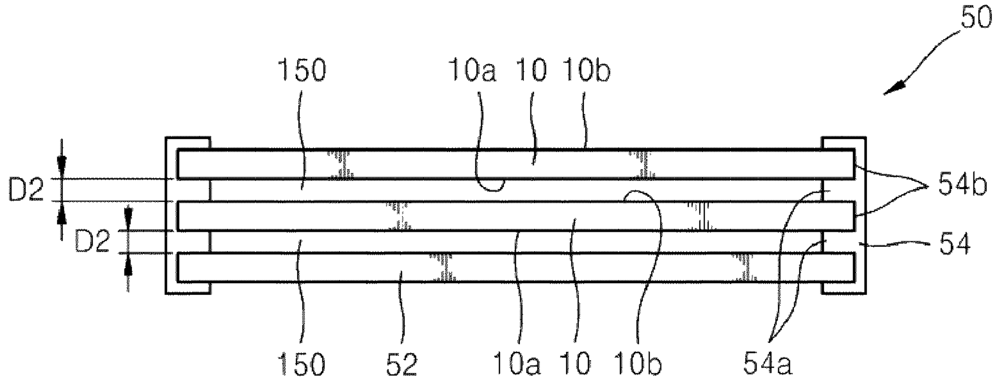

FIG. 11 is a top plan view illustrating a slide module 50 in which two slides are mounted, according to another embodiment of the invention.

Referring to FIG. 11, the slide module 50 according to the current embodiment may include a slide cover 52 and a slide clip 54. At least two slides 10 may be mounted on the slide module 50. Thus, the slide clip 52 may include a plurality of clip air gap portions 54*a* corresponding to the number of slides 10 mounted on the slide module 50. In addition, the slide clip 52 may include a plurality of second slots 54*b*. The number of the second slots 54*b* is equal to the sum of the number of slides 10 mounted on the slide module 50 and the number of slide covers 52.

As illustrated in FIGS. 8 through 11, the slide module 50 may be configured so that a first side 10*a* of one or more slides 10 can contact the reaction space 150.

According to a slide processing apparatus 1 illustrated in FIGS. 1 through 11, all of the slides 10 to which a bio probe is attached can be simultaneously processed. In particular, a reaction sample may be injected into the reaction space 150 so that the amount of the reaction sample can be minimized. In addition, a reaction occurs when at least four sides of each slide 10 is encompassed by the reaction heating plates 120 and the side wall heating plates 104 so that temperature management including temperature control and maintenance can be easily performed.

It should be understood that these exemplary embodiments described therein should be considered in a descriptive sense only and not for purposes of limitation. Descriptions of features or aspects within each embodiment should typically be considered as available for other similar features or aspects in other embodiments of the invention.

What is claimed is:

1. A slide processing apparatus for processing a plurality of slides to which a bio probe is attached, the slide processing apparatus comprising:

a reaction chamber of which side walls are sealed and including a side wall heating plate inside the side walls of the reaction chamber; and a plurality of reaction heating plates disposed in parallel in the reaction chamber at a first distance from each other, wherein the side wall heating plate and each reaction heating plate are connected to each other, wherein the reaction chamber is adapted to receiving a plurality of slides mounted adjacent to the reaction heating plates and in parallel to the reaction heating plates.

2. The slide processing apparatus of claim 1, wherein each slide of the plurality of slides comprises a first side and a second side opposite to the first side, wherein said first side is adapted to having a bio probe attached thereto.

3. The slide processing apparatus of claim 2, wherein the first side of each slide is adjacent one of the reaction heating plates.

4. The slide processing apparatus of claim 2, wherein each slide is mounted adjacent to one side of each reaction heating plates so that the first sides of the slide extends in the same direction as the reaction heating plate.

5. The slide processing apparatus of claim 1, wherein the reaction chamber further comprises a first slot in which each of the slides is mounted inside the side walls of the reaction chamber.

6. The slide processing apparatus of claim 5, wherein a pair of first slots are disposed facing each other in two opposite inside areas of the side walls of the reaction chamber.

7. The slide processing apparatus of claim 1, further comprising a fixing portion attached to each of the reaction heating plates, wherein said fixing portion fixes each slide.

8. A slide processing apparatus for processing a plurality of slides to which a bio probe is attached, the slide processing apparatus comprising:

a reaction chamber of which side walls are sealed;

a plurality of reaction heating plates disposed in parallel in the reaction chamber at a first distance from each other; and a plurality of slide modules adapted to mounting one or more slides, wherein said reaction chamber is adapted to receiving the plurality of slide modules mounted adjacent to the reaction heating plates in the reaction chamber and in parallel to the reaction heating plates, wherein each slide module comprises:

a slide cover disposed adjacent to a first side of a slide that is to be mounted on the slide module; and a slide clip supporting the slide and the slide cover on both ends of each slide module, and including a slot in which the slide and the slide cover are mounted at a second distance from each other, wherein each slide module is mounted wherein a second side of a slide mounted on the slide module is directed toward the reaction heating plates.

9. The slide processing apparatus of claim 8, wherein said first side of each slide is adapted to having a bio probe attached thereto.

10. The slide processing apparatus of claim 8, wherein each slide module further comprises a spacer disposed between the slide and the slide cover wherein the slide and the slide cover can be disposed in parallel at the second distance from each other.

11. The slide processing apparatus of claim 8, wherein a plurality of slides are mounted in each slide module; and the first sides of the slides are placed in parallel in the same direction as the slide module.

12. The slide processing apparatus of claim 8, wherein a reaction space is encompassed by the slides, the slide cover, and the slide clip, and has a volume of about 10 μl to about 1 ml.

13. The slide processing apparatus of claim 8, wherein the first distance is about 0.5 cm to about 2 cm.

14. A slide processing apparatus for processing a plurality of slides to which a bio probe is attached, the slide processing apparatus comprising:

a reaction chamber with sealed side walls for receiving a plurality of slides, and a side wall heating plate inside the side walls of the reaction chamber; and a plurality of reaction heating plates disposed in parallel in the reaction chamber at a first distance from each other, wherein the side wall heating plate and each reaction heating plate are connected to each other; and a first slot in the side walls of the reaction chamber for mounting slides.

15. The slide processing apparatus of claim 14, wherein the reaction chamber is adapted to receiving a plurality of slides mounted adjacent to the reaction heating plates and in parallel to the reaction heating plates.

* * * * *